(12) United States Patent
Kuhr et al.

(10) Patent No.: US 7,785,338 B2
(45) Date of Patent: Aug. 31, 2010

(54) LANCING AID COMPRISING A LANCET SYSTEM THAT IS PROTECTED AGAINST RE-USE

(75) Inventors: Hans-Juergen Kuhr, Mannheim (DE); Thomas Weiss, Mannheim (DE); Richard Forster, Fensterbach (DE); Peter Sachsenweger, Zeitlarn (DE); Karl-Peter Ebert, Fraenkisch-Crumbach (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 654 days.

(21) Appl. No.: 10/806,483

(22) Filed: Mar. 22, 2004

(65) Prior Publication Data
US 2004/0260325 A1    Dec. 23, 2004

(30) Foreign Application Priority Data
Mar. 20, 2003    (DE) .................... 103 12 357

(51) Int. Cl.
*A61B 5/151* (2006.01)
(52) U.S. Cl. .................... 606/181; 606/182; 606/183
(58) Field of Classification Search .................. 606/181, 606/182, 183, 185, 167; 604/197, 198; 76/119; 600/583; 79/119
See application file for complete search history.

(56) References Cited

U.S. PATENT DOCUMENTS

| | | | | |
|---|---|---|---|---|
| 4,442,836 A | | 4/1984 | Meinecke et al. ........... 128/314 |
| 4,817,603 A | | 4/1989 | Turner et al. ............ 128/329 R |
| 4,974,879 A | | 12/1990 | Berch et al. .................. 285/158 |
| 4,990,154 A | | 2/1991 | Brown et al. ................. 606/182 |
| 5,074,872 A | | 12/1991 | Brown et al. ................. 606/182 |
| 5,152,775 A | * | 10/1992 | Ruppert ....................... 606/182 |
| 5,207,699 A | | 5/1993 | Coe ............................ 606/182 |
| 5,314,442 A | * | 5/1994 | Morita ........................ 606/182 |
| 5,324,303 A | | 6/1994 | Strong et al. ................. 606/181 |
| 5,385,571 A | | 1/1995 | Morita ........................ 606/181 |
| 5,423,847 A | * | 6/1995 | Strong et al. ................. 606/182 |
| 5,454,828 A | | 10/1995 | Schraga ...................... 606/181 |
| 5,554,166 A | | 9/1996 | Lange et al. |
| 5,611,809 A | | 3/1997 | Marshall et al. ............. 606/181 |
| 5,628,764 A | | 5/1997 | Schraga ...................... 606/182 |
| 5,628,765 A | | 5/1997 | Morita ........................ 606/182 |
| 5,797,942 A | * | 8/1998 | Schraga ...................... 606/182 |
| 5,964,731 A | | 10/1999 | Kovelman ................... 604/110 |
| 6,168,606 B1 | * | 1/2001 | Levin et al. .................. 606/181 |
| 6,719,771 B1 | * | 4/2004 | Crossman ................... 606/181 |
| 6,783,537 B1 | * | 8/2004 | Kuhr et al. ................... 606/182 |
| 2002/0077650 A1 | * | 6/2002 | Schraga ...................... 606/182 |
| 2002/0128608 A1 | * | 9/2002 | Teo et al. ..................... 604/198 |

(Continued)

FOREIGN PATENT DOCUMENTS

DE       100 53 974       10/2000

(Continued)

*Primary Examiner*—Anhtuan T Nguyen
*Assistant Examiner*—Amy T Lang
(74) *Attorney, Agent, or Firm*—Bose McKinney & Evans LLP

(57) ABSTRACT

The present invention is generally directed towards the field of lancing aids in which disposable lancet systems are used. The lancet system according to the invention has a needle body which surrounds the needle tip in a lancet system in a protective manner and also comprises a protection against re-use of an ejected lancet system.

53 Claims, 10 Drawing Sheets

U.S. PATENT DOCUMENTS

2003/0114839 A1* 6/2003 Looper et al. ............... 606/1
2005/0015020 A1* 1/2005 LeVaughn et al. .......... 600/583

FOREIGN PATENT DOCUMENTS

| EP | 0 565 970 | 4/1993 |
| EP | 0 595 148 | 10/1993 |
| EP | 0 630 609 | 6/1994 |
| EP | 0630609 A2 | 6/1994 |
| JP | 6-114039 | 4/1994 |
| WO | WO 91/11212 | 8/1991 |
| WO | WO 00/02482 | 1/2000 |
| WO | WO 01/66010 | 9/2001 |
| WO | WO 02/36010 | 5/2002 |

* cited by examiner

Fig. 2
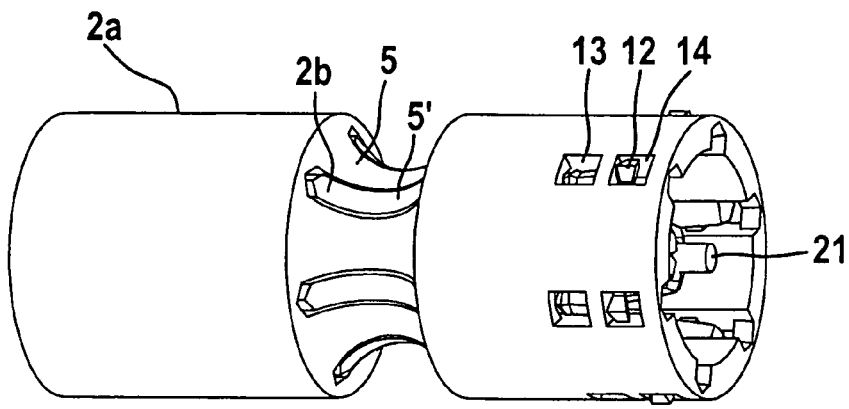
a)
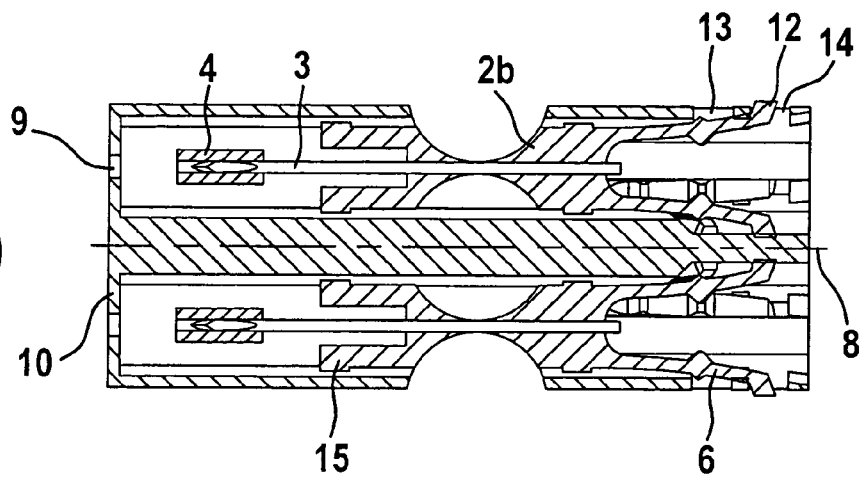
b)
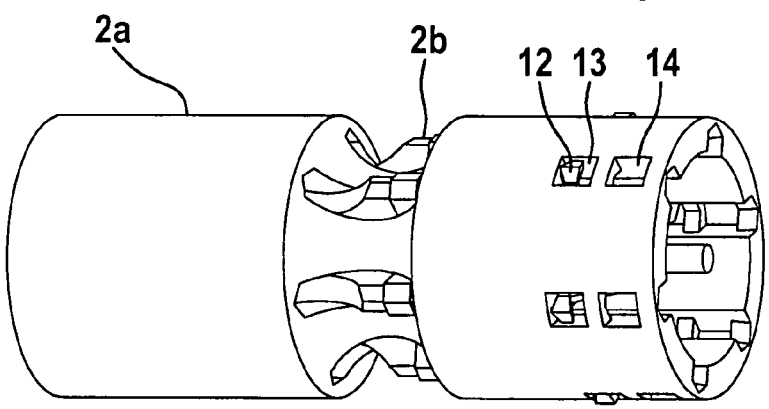
c)
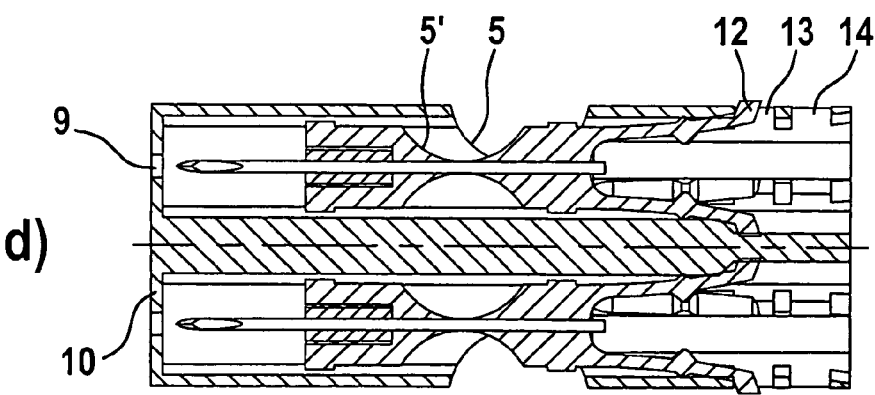
d)

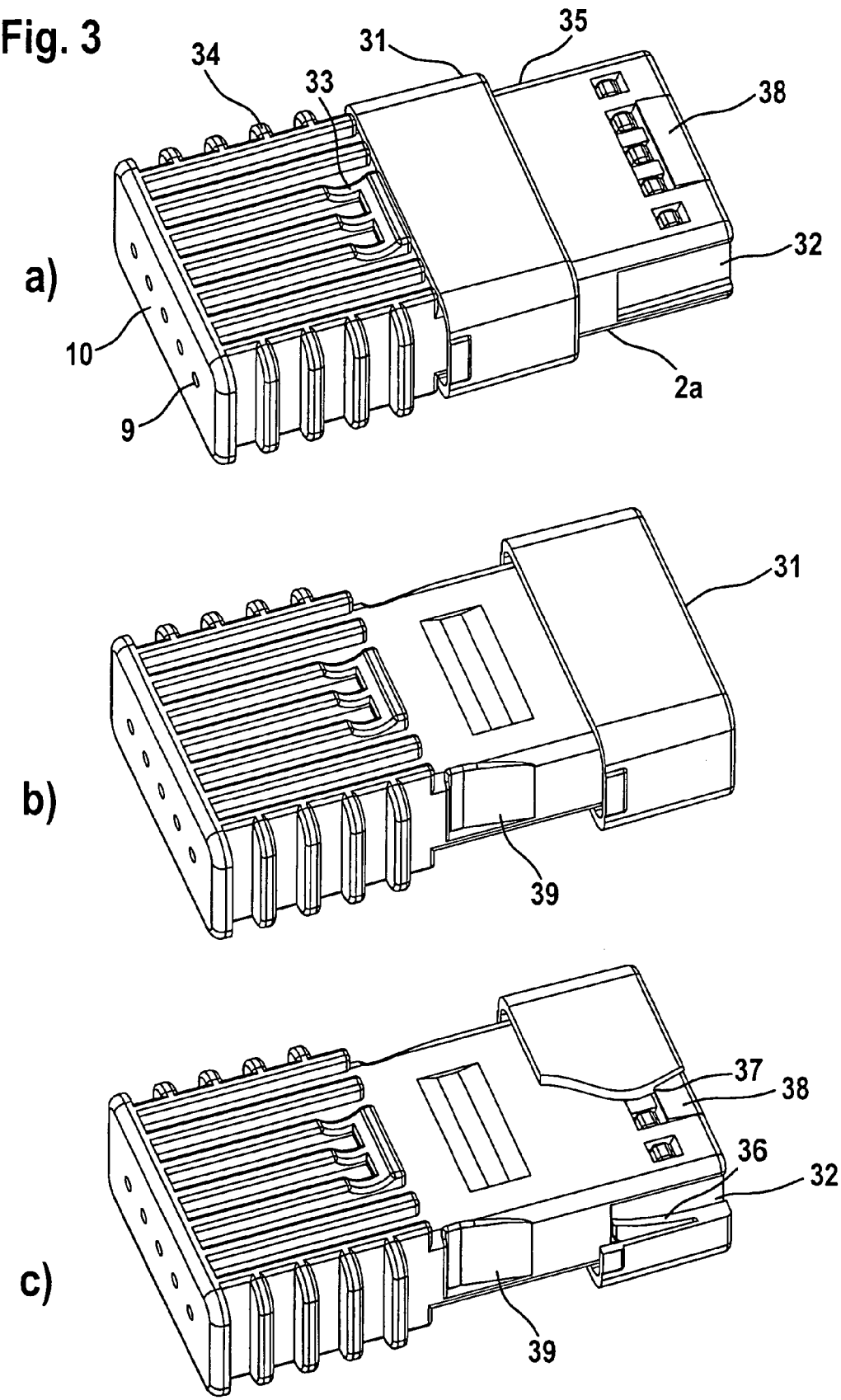

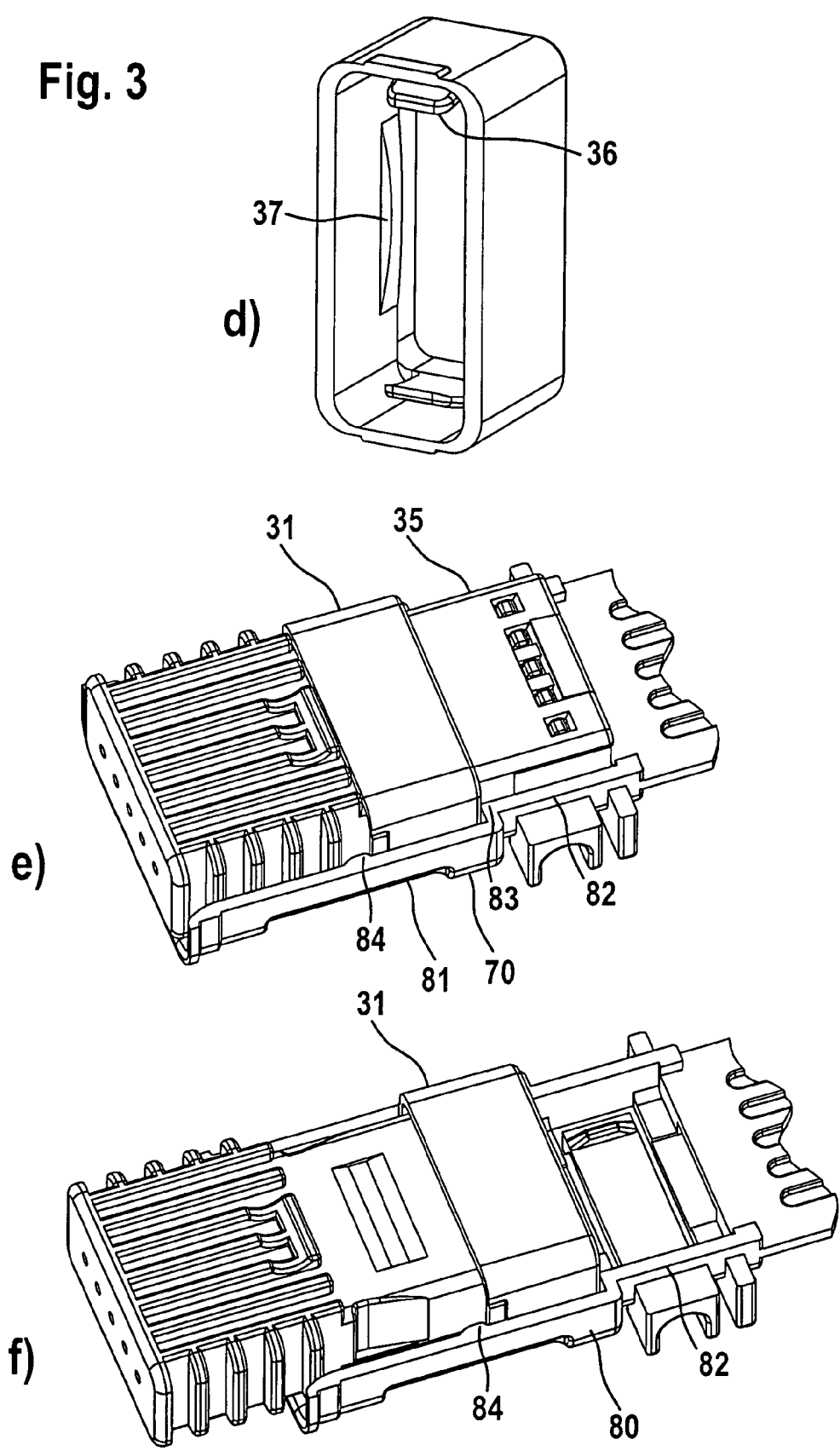

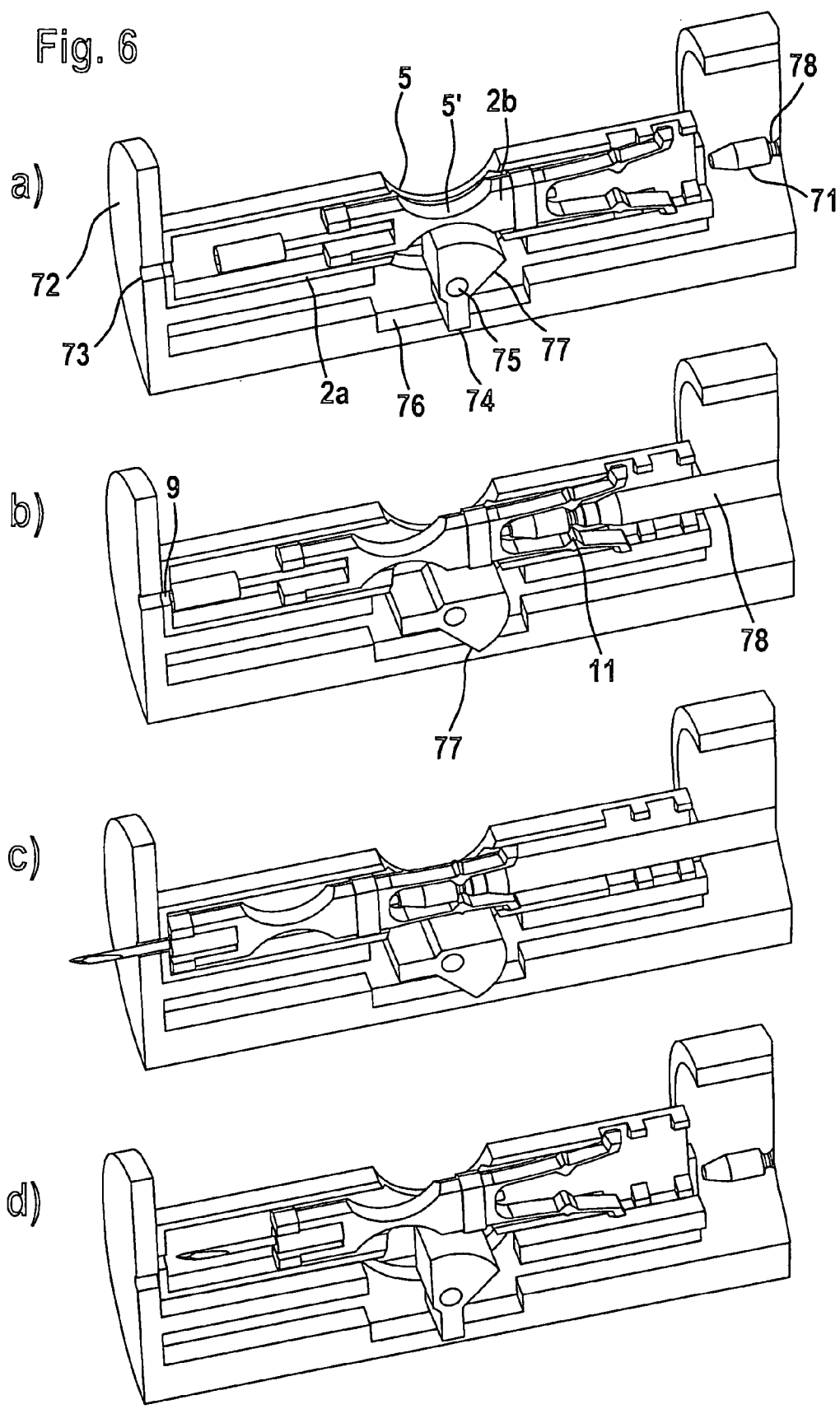

Fig. 7
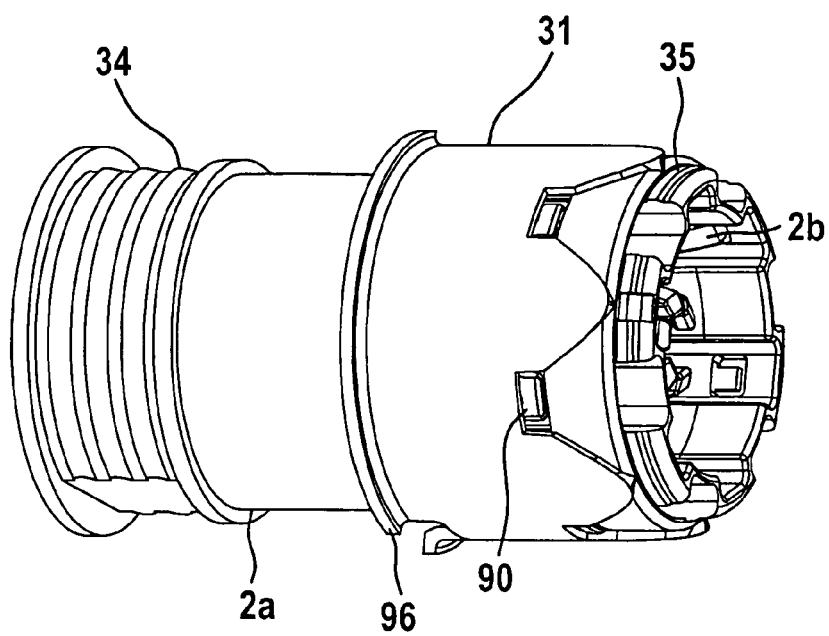
a)
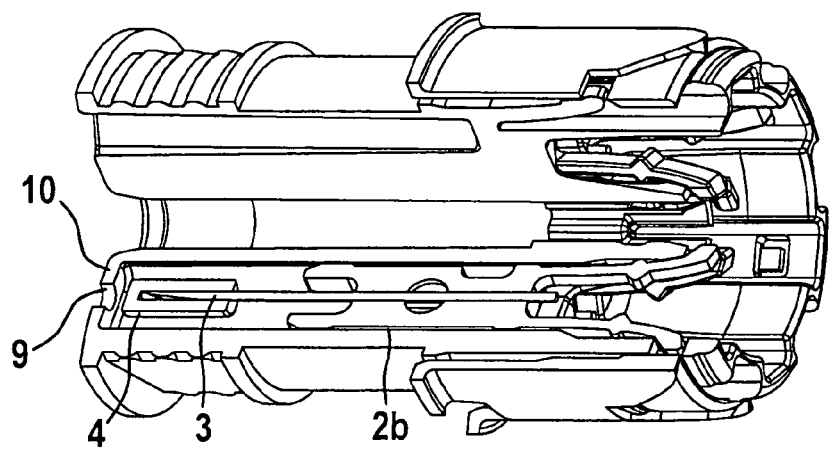
b)
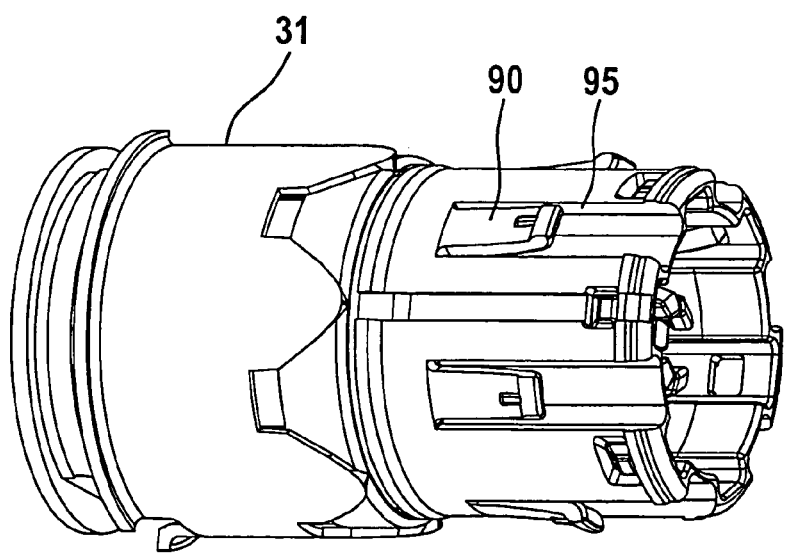
c)

Fig. 7
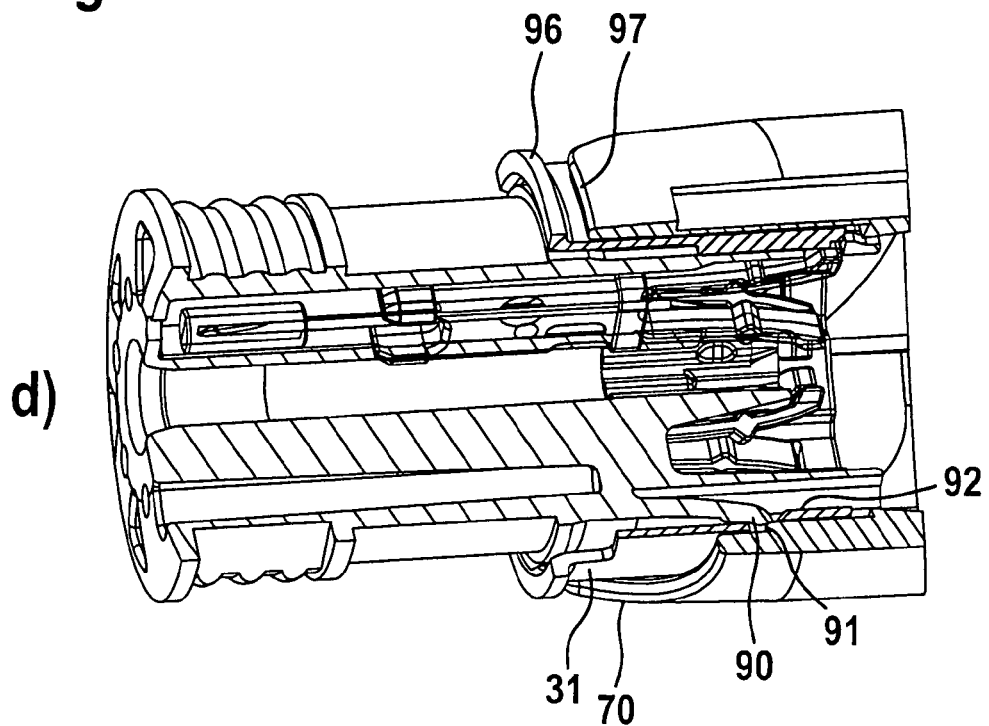
d)
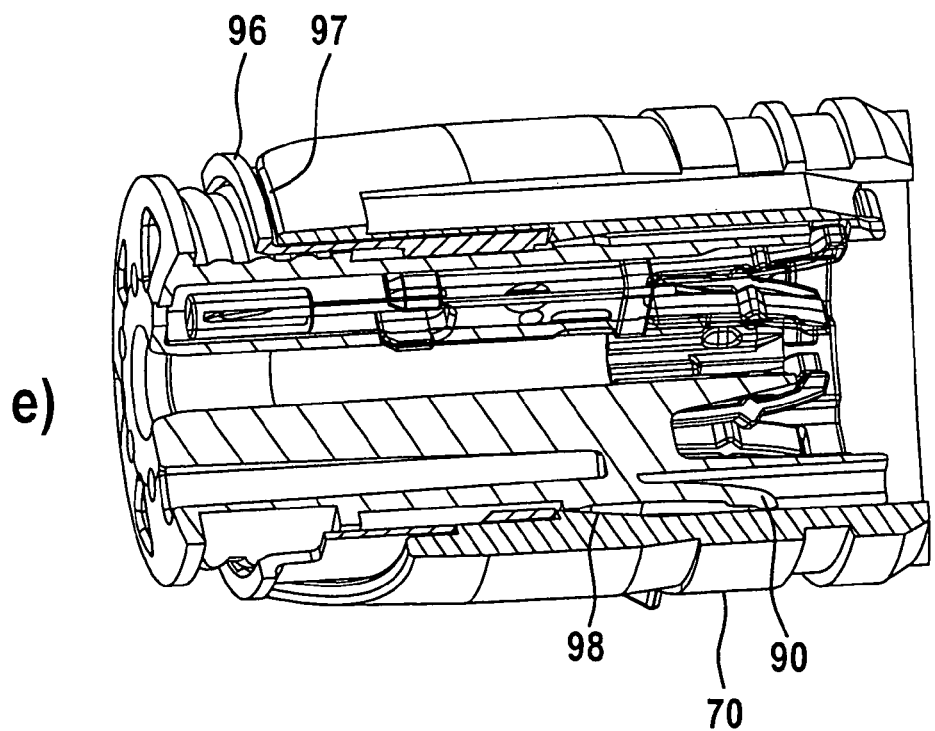
e)

LANCING AID COMPRISING A LANCET SYSTEM THAT IS PROTECTED AGAINST RE-USE

PRIORITY CLAIM

This application claims priority to German Application Number DE 103 12 357.1 filed Mar. 20, 2003.

TECHNICAL FIELD

The invention concerns a lancet system that can be used in a lancing aid for withdrawing blood for diagnostic purposes.

BACKGROUND AND SUMMARY

In a variety of diseases it is necessary to examine human blood for an analyte contained therein. In many cases this only requires the withdrawal of a small amount of blood in the form of a blood drop by producing a small puncture wound. A particularly important example of such a case is diabetes in which the glucose content of blood has to be examined at regular intervals. Blood may also for example be examined with regard to coagulation parameters, triglycerides, HbA1c or lactate. Blood lancet devices which consist of a lancing aid and a tailor-made replaceable lancet are usually used to produce the required puncture wounds. The housing of the lancet instrument contains a lancet holder in which one interchangeable lancet can be inserted. During the lancing operation the lancet holder is rapidly moved in a lancing direction by a lancet drive of the lancet which is also integrated into the lancing aid until the needle tip emerges from an exit opening provided at the front end of the lancing aid and produces a small puncture wound in the part of the body that is pressed against the front end. Afterwards the lancet holder containing the lancet is moved back in the opposite direction to lancing.

Small, easy-to-handle blood collection devices, so-called lancing aids that can be easily and reliably operated by the user and enable a part of the body to be lanced in an almost painless manner are now routinely used. In order to avoid infections especially in hospitals, the lancets are disposable elements intended for single use. After a lancet has been used once, the lancet is removed after the lancing operation or ejected from the device and discarded as refuse. In such a case the exposed needles in a refuse container may lead to injury during waste disposal resulting in a contamination of other persons by the used lancet. Such contamination may lead to infections and thus some countries are planning to impose a ban on blood collection systems in which the needle tip is freely accessible after use. In addition to a risk of injury during waste disposal there is also a risk that a used lancet may be accidentally re-used. This is particularly relevant for hospitals in which a lancing aid is used for several patients since such inadvertence of the nursing staff could lead to a patient being contaminated with the blood of a previous patient.

In addition to the use of blood lancet devices by medical staff, lancing aids are also used by laymen in the so-called home-monitoring field. This is particularly the case for monitoring the treatment of diabetics. Thus it has been found in the treatment of diabetics that serious damage associated with diabetes such as loss of sight can be substantially reduced when the glucose concentration in the blood of the diabetic is determined frequently and up to five times daily and the insulin injection is exactly adjusted on the basis of these measurements. Lancing aids which enable the diabetic to carry out such a blood examination are used for home-monitoring in order to carry out such frequent measurements. The resulting requirements for a blood lancet device are a simple handling when inserting new lancets and a reliable ejection of used lancets in addition to a simple handling when triggering the lancing operation and a relatively painless puncture. Lancet replacement should on the one hand be as simple as possible and, on the other hand, ensure the utmost safety with regard to unintentional injury of the user or other persons. Although in the home-monitoring field it is conceivable that a lancet, once inserted, is used several times for lancing by the same user, even in this case an accidental re-use of an ejected lancet should be prevented once the user has decided to discard the lancet. Furthermore other persons in particular should be reliably protected from the discarded lancets for example during waste disposal.

In the prior art the tip of the needle is usually surrounded by a tip cover made of plastic when the lancet is inserted which allows a safe insertion of the lancet. When the lancet is inserted, the tip cover is removed to expose the sharp tip of the needle for the lancing operation (U.S. Pat. No. 5,628,765). However, due to the exposed needle tip there is a risk of accidental injury and the tip may become damaged. The lancet is removed from the lancing aid after one or several lancing operations. This can either be carried out manually in which case there is a high risk of injury by the needle tip or by an automatic ejection mechanism.

A blood lancet device is disclosed in the patent EP 0 565 970 in which the lancet is ejected from the lancet holder by means of an ejecting rod. The user can operate the ejecting rod by pressing a corresponding button.

Furthermore an ejecting mechanism is described in the patent document U.S. Pat. No. 4,442,836 where the needle is automatically released when the lancing aid is retensioned so that the used lancet is discarded after each lancing operation. Such ejecting mechanisms require a relatively high degree of additional engineering. Moreover multiple use of an already inserted lancet system is not possible which is, however, often desired by customers especially in the home-monitoring field. Another major disadvantage of the described prior art is that the needle tip is unprotected after the lancet has been ejected resulting in a risk of injury as described above.

In order to facilitate the safe removal of a used lancet, blood collection systems are also described in the prior art which ensure the needle tip is protected after ejecting the lancet. This is regarded as an important feature especially for elderly users or those that are handicapped by poor sight and shaking hands as a result of disease.

A protection of the needle tip is achieved in the prior art by integrating the lancet in a cap of the lancing aid such that the lancet and the housing cap together form a replaceable disposable unit. Such designs are described in the documents EP 0595148 and U.S. Pat. No. 4,990,154, U.S. Pat. No. 5,454,828 and DE 10053974. When the lancet is ejected by the user, the housing cap is placed over the needle tip so that the lancet surrounded by the cap can be subsequently discarded. Even if the needle tip is protected after ejection by the described mechanism, it is nevertheless possible for a careless user to reinsert a needle that has already been ejected once and carry out a new lancing operation. Consequently the user is instructed to recognize that the needle has already been used.

Only the document EP 0 630 609 discloses a mechanism which directly prevents reinsertion and thus re-use of a lancet that has been ejected once. The described lancet device comprises a needle with a needle body which breaks when the needle is ejected from the lancing aid to prevent a reinsertion of the needle. This prevents the user from re-using a contaminated needle. However, a disadvantage of the prior art is that the needle tip is unprotected after the needle has been ejected.

The object of the invention is to provide an easy-to-use lancing aid preferably for the home-monitoring field which prevents re-use of an already ejected lancet system and also ensures a protection from injury by the needle tip after the lancet system has been ejected. It should advantageously be possible to easily reuse a needle of a lancet system that has been inserted once.

The object is achieved by a lancing aid and a lancet system according to the independent claims. Preferred embodiments are derived from the dependent claims.

The invention concerns a lancet system and a lancing aid containing the lancet system. The lancing aid has a housing for inserting a lancet system. The housing also has an opening where the needle tip can emerge from the housing and a drive mechanism for carrying out a lancing operation.

According to the invention the housing additionally has a holding element which can interact with a corresponding holding element of the lancet system as soon as the lancet system has been inserted in the lancing aid. The interaction between the holding elements enables the lancet system to be positioned in the housing at a defined site. An exact positioning of the lancet system is important especially with regard to the drive mechanism for the lancing aid since it is the only way in which the needle can be correctly coupled to the drive mechanism such that the needle can perform a lancing operation at high speed and almost without vibration. This enables a rapid and relatively painless puncture in the intended part of the body. In addition to the described holding element, the lancet system for the lancing aid comprises at least one needle with a tip which is suitable for producing an opening in the skin. The needle is connected to a needle housing and at least one protective portion of the needle housing and the needle can be moved relative to one another. In a first position the needle tip is at least partially surrounded by the protective portion of the needle housing whereas in a second position the protective portion of the needle housing and the needle tip are disposed relative to one another such that the needle tip is released from the protective portion of the needle housing. If the protective portion of the needle housing is in its first position, it thus guards against injury by the lancet tip which is particularly important after the lancet system has been ejected from the lancing aid.

The needle housing also contains a blocking mechanism which is activated by an interaction with the lancing aid. The blocking mechanism changes the needle housing in such a manner that after the lancet system has been ejected from the lancing aid, the holding element on the lancing aid can no longer interact with the holding element of the lancet system when it is reinserted. This prevents re-use of a lancet system that has been ejected once. In this connection the blocking mechanism can be automatically actuated as soon as certain operating steps have been carried out on the lancing aid. However, other embodiments are conceivable in which the user actuates the blocking mechanism by a separate operating step.

As a result of the special design of the needle housing, the lancet system according to the invention provides a protection from the needle tip such that after ejection from the lancet system the tip is surrounded by the protective portion of the needle housing to such an extent that injury by the tip is prevented. The blocking mechanism also influences the interaction of the holding elements. Within the scope of the invention the term interaction of the holding elements encompasses any conceivable embodiment that is known in the prior art for inserting and positioning a lancet or a magazine in a lancing aid. For example the holding elements can be snapped in or clamped. Suitable holding elements for this may for example be designed as locking lugs, grooves or hooks to name only a few possible embodiments. Similarly to the systems described in the prior art containing individual lancets, it is also conceivable that the lancet system is already adequately positioned and held in the lancing aid due to its coupling to the drive unit so that for example the drive unit itself can be used as a holding element for an appropriately designed lancet system.

If several holding elements are provided to position the lancet system, the blocking mechanism advantageously prevents an interaction between the holding elements of the lancet system and the lancing aid so that the lancet system cannot be held and positioned in the lancing aid. This is particularly advantageous when the lancet system and lancing aid each have several holding elements that act independently of one another.

In a preferred embodiment the interaction of the holding elements is blocked in such a manner that the lancet system is prevented from being reinserted in the lancing aid. Within the scope of the invention the term "reinsertion" encompasses a handling of the lancet system such that the lancet system is positioned at the position in the lancing aid intended for carrying out the lancing operation and is held there due to the interaction of the holding elements. For this purpose the lancet system is again used at its original position in the lancing aid thus restoring the original state of the lancet system and lancing aid which was present when the lancing aid was first used.

When operating the lancing aid, the user can advantageously immediately and unambiguously identify an already used lancet system for example due to the fact that a reinsertion of the lancet magazine into the lancing aid is blocked. Hence in contrast to the prior art the user is not required to consciously distinguish between a used lancet system and a new lancet system. Advantageously the user is spared an unnecessary reinsertion of a used lancet system which no longer functions which elderly and visually handicapped persons often find to be difficult.

However, it is also possible that the blocking mechanism only blocks the lancing operation in which case it is possible to reinsert a needle that has already been ejected. If a reinsertion of the lancet system is prevented, this usually means that the lancet system cannot couple to the drive unit.

In a preferred embodiment the blocking mechanism is essentially achieved by a change in the shape of the needle housing. This proves to be particularly advantageous when the shape of the needle housing itself forms at least a part of a holding element. It is also possible that a deformation of the needle housing spatially separates the holding elements in the lancing aid such that the blocking mechanism has an indirect effect on a holding element without directly acting on it. Hence the lancet system can no longer be positioned and held at a defined position in the lancing aid. In a preferred embodiment the deformation of the needle housing transfers the protective portion of the needle housing to a first position such that there is no risk of injury when disposing a used lancet. The protective portion of the needle housing and the blocking mechanism are then achieved as a single component of the lancet system.

In principle the holding elements can interact in a variety of ways. The blocking mechanism may have a direct or indirect effect on the holding elements. In the case of a direct effect on the holding elements, at least one holding element is advantageously changed, covered or destroyed in such a manner that interaction of the holding elements is no longer possible.

Furthermore embodiments are also conceivable in which the lancet system is positioned within a lancing aid due to magnetic properties of the system. Hence a change in the magnetic properties of the needle housing could prevent a re-use of the lancet system. Appropriate magnetic elements of the needle housing or lancing aid are then the holding elements of the system.

Since the blocking mechanism advantageously only prevents a repeated insertion of the lancet system but does not prevent re-use of a needle that has already been inserted, the lancet system also satisfies requirements in the home-monitoring field where multiple use of a once inserted needle is often desired.

The lancing aid according to the invention for collecting blood has a drive unit with a plunger which moves a needle from its resting position into a lancing position. A number of drive mechanisms are known in the prior art that can be used in the field of blood collection devices (e.g. U.S. Pat. No. 5,314,442, WO 00102482, U.S. Pat. No. 3,030,959). In particular drive mechanisms are frequently used which draw their energy from a previously tensioned spring. Drive units are preferably used within the scope of the present invention which enable a guided movement of the plunger and needle for example as a result of a form-fitting coupling as described in the document DE 10053974. Guided movements of the needle for example by means of guide blocks have also been previously described in EP 0 565 970. Such drive mechanisms are preferred because the puncture is less painful. However, the system according to the invention is not limited to a particular drive mechanism, but on the contrary, can be combined with a variety of drive units.

An important aspect of the invention is a lancet system that can be detached from the drive unit containing at least one needle where the lancet system is provided as a disposable unit. In this connection the term needle encompasses a blade-shaped substantially flat lancing unit and all other conceivable embodiments thereof. In principle needles can be used for the invention that are basically well known in the prior art and can be used in a lancet system. In the prior art a needle is often combined with a base body that can couple to the lancing aid which is referred to as a lancet. Such lancets often have a base body made of plastic in which a metal needle is disposed. According to the invention it is possible to integrate such a lancet into the lancet system according to the invention. It is for example conceivable that the needle housing according to the invention contains a base body like that used for lancets in the prior art, where the inventive functionality of the system is maintained by integration of the base body. In this case the lancet system has an at least two-part design according to the described embodiment. In a preferred embodiment the needle housing is designed such that a plurality of lancets is disposed in the needle housing such that the needle housing represents a magazine containing a plurality of lancets and each base body of the lancet represents a needle body. Consequently in a preferred embodiment the protective portion of the needle housing is formed by the magazine housing. The needle and the base body can then be guided in a movable manner within the magazine. The needles within a needle housing designed according to the invention as a magazine are preferably present in separate chambers in order to prevent contamination of unused needles by used needles when reloading.

In order to carry out a lancing operation, portions of the needle body are advantageously designed like the system already described in DE 10053974 such that the individual needles of the system can be actively coupled to the drive unit of the lancing aid. Embodiments that can also be used to drive needles within a magazine of a lancing aid are described for example in the documents DE 10053974, U.S. Pat. No. 4,990,154 and U.S. Pat. No. 5,074,872. The chambers arranged next to one another in which the lancets are individually located are positioned successively relative to the drive unit in order to carry out a lancing operation in such a manner that in each case a single needle can be coupled to the plunger of the drive unit. Also in this case magazines in the form of a drum containing chambers in which the needles are located parallel to the longitudinal axis of the drum have also proven to be particularly advantageous.

The lancet system also advantageously comprises a needle housing which at least partially surrounds the needle tip by the protective portion of the housing when the needle is in its resting position. In order to carry out the lancing operation, the protective portion of the needle housing is spatially separated from the needle tip so that the protective portion of the needle housing does not hinder the lancing operation. When the lancet system is ejected from the lancing aid the needle remains in its resting position so that the ejected needle tip is protected and additionally the blocking mechanism according to the invention prevents a re-use of the lancet system. It is, however, also possible that the protective portion of the needle housing is not transferred to its first position until the lancet system is ejected so that the needle tip is only protected as a result of the ejection. In a preferred embodiment an unused needle is also in a resting position before insertion into the lancing aid to prevent injury by the needle tip and contamination when the needle is inserted as well as after ejection.

A blocking mechanism according to the invention can be actuated for example when the lancet system is ejected from or inserted into the lancing aid independently of the needle tip protection. In principle the blocking mechanism or the needle tip guards can also be activated separately or by means of individual operating steps of the lancing aid e.g. during the lancing operation. In general all possible combinations are conceivable which ensure a simultaneous or successive blocking mechanism and protection of the needle tip.

The blocking mechanism can have a variety of designs but it is advantageous that the shape of the needle housing is changed in such a manner that it is no longer possible to reinsert a lancet system once it has been ejected. For example the blocking mechanism can move at least one part of the needle housing that interacts with the lancing aid in such a manner that a change in its position blocks a reinsertion of the lancet system. This is for example the case when the blocking mechanism closes a recess in the needle housing which forms a holding element or a recess is generated in the needle housing that is essential for an interaction of the lancet system with a lancing aid. Furthermore it is also possible that the blocking mechanism comprises a predetermined breaking point which results in a breaking of the needle housing when the lancet system is ejected. It is also conceivable that the needle housing is enlarged, made smaller or bent which are only a few methods for deforming the needle housing.

According to the invention an interaction between the lancet system and lancing aid activates the blocking mechanism and sets a first position of the protective portion where the protective portion at least partially surrounds the needle tip.

An important requirement for the lancet system is that the needle tip that is used to produce a wound in an appropriate part of the body is sterile. The sterility of the needle tip has to be ensured over a long period which extends from the manufacture of the lancet system up to its use. Sterility can be achieved during the manufacture of the lancet system by for example gamma radiation which is commonly used in the prior art. In order to maintain sterility, the lancet system can be sealed in a wrapping, for example a polyethylene bag. In another embodiment the opening of the lancet system where the needle tip emerges from the protective portion of the needle housing can for example be closed by a sealing foil. These are preferably detachable sealing foils which the user removes before using the lancet system. However, it is also possible to use thin foils which are not pierced by the needle tip until the needle is used so that the user does not have to carry out additional handling steps. Such foils may already be used as an integral part of the manufacturing process for the lancet system which is usually by means of an injection moulding process.

Furthermore in the prior art an elastomer is described in the application WO 01/66010 for sterile protection which encloses the needle tip and thus protects it against contamination. This sterile protection can either be pierced during the lancing operation or be removed by the operator before use.

In another advantageous embodiment the protective portion of the needle housing can comprise a sterile protection and/or the protective portion can be essentially formed thereby. In this case the elastomer of the sterile protection serves for example as the protective portion of the needle housing by the fact that the needle tip can be moved in a guided manner relative to the elastomer. Another part of the needle housing that can be actuated independently of the sterile protection is able to change the needle housing and represents the blocking mechanism. This requires that the sterile protection can reversibly expose the needle tip and surround it again which is for example the case with an elastomer protection (WO 01/66010) in which the elastomer is firstly pierced during the lancing operation and subsequently the needle tip is retracted into the elastomer. Consequently in this example the needle tip changes its position relative to the sterile protection during the lancing operation and the needle tip is protected by the sterile protection in its resting position after the lancing operation. In principle many embodiments of a sterile protection are conceivable and hence the inventive system is not limited to any special embodiment of a sterile protection.

Further features and advantages of the invention will become apparent from the following discussion and the accompanying drawings in which: The system according to the invention is illustrated in the following on the basis of the figures and examples without being thereby limited to the individual examples.

BRIEF DESCRIPTION OF THE DRAWINGS

FIG. 1 (e) illustrates a breaking of the needle housing when the lancet system is ejected from the lancing aid;

FIG. 2 (a) to FIG. 2 (d) is a perspective view of the Lancet system in which the blocking mechanism is activated during the lancing operation;

FIG. 3 (a) to FIG. 3 (f) is a perspective view of the blocking mechanism that is activated when the system is ejected;

FIG. 7 (a) to FIG. 7 (e) is a perspective view of the Lancet system with a blocking mechanism which widens the needle housing.

DETAILED DESCRIPTION

The following description of the preferred embodiment is merely exemplary in nature and is in no way intended to limit the invention or its application or uses.

Figure 1:
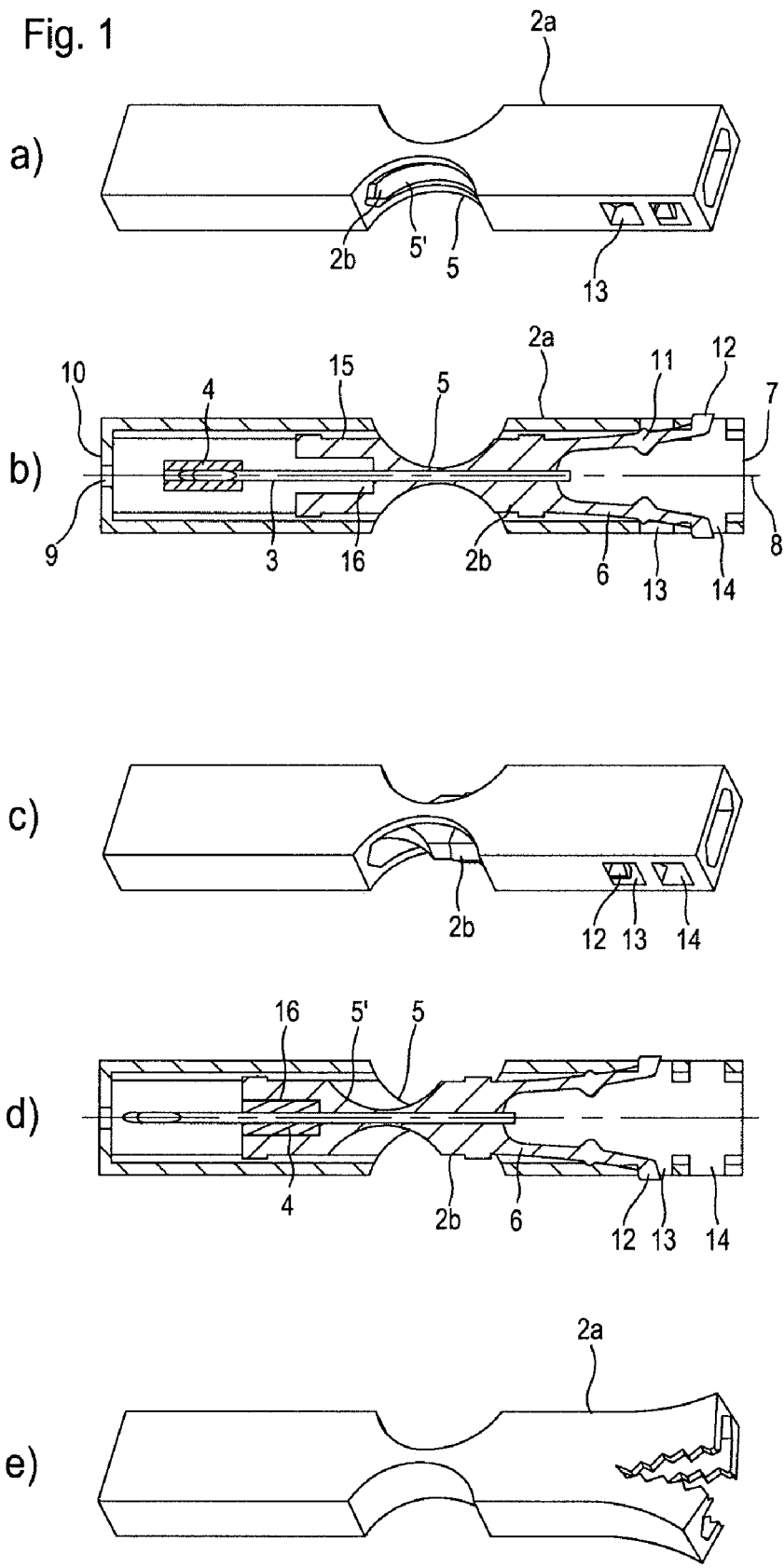
FIG. 1 (a) to FIG. 1 (d) is a perspective view of a two-part lancet system.

FIG. 1 shows a lancet system (1) which is essentially in two parts. FIGS. 1b and 1d each show a cross-section through the lancet system shown in FIGS. 1a and 1c before and after use respectively. The system has a needle (3), the front tip of which is wrapped in a sterile manner with an elastomeric protection (4). Such elastomers which ensure the sterility of the needle tip are known for example from the document WO 01/66010 to which reference is herewith made. The metallic needle (3) is attached to a plastic body (2b) and is permanently connected thereto. The plastic body has a rear portion (6) which couples the lancet system to a drive plunger such that the needle can be moved along the axis (8) in the direction of lancing. The rear portion (6) of the plastic body which is a part of the needle body comprises two arms which can connect in a form fitting manner during the lancing operation with a drive plunger of a lancing aid (not shown) by means of the projecting parts (11). A form-fitting connection between a drive plunger and lancet is described for example in the document DE 10053974 to which reference is also herewith made. Of course any other coupling mechanism that is described in the prior art is conceivable for carrying out the lancing operation. The needle (3) and the plastic body (2b) that is permanently connected thereto are movably mounted in the plastic housing (2a) which represents the protective portion. The needle and needle body (2b) can be moved within this needle housing along the direction of lancing. The protective portion of the needle housing (2a) has a lower wall (10) which has a hole (9) through which the needle tip can emerge during the lancing operation. The needle housing also has an opening (7) at its upper end through which a drive plunger of a lancing aid can be inserted into the needle housing in order to connect in a form-fitting manner with the needle body and perform the lancing operation. The protective portion of the needle housing (2a) also has two recesses (13 and 14) which allow it to be locked into the needle body (2b). In order to enable the needle body to engage in the protective portion, the rear portion (6) of the needle body also has locking lugs (12) which engage in the recesses (14) in a first resting position of the lancet system before use and hold the needle body due to the spread arms (6). The middle portion of the protective portion and of the needle body have trough-shaped taper (5 and 5') such that the tapered parts (5 and 5') exactly fit together in the first resting state before the lancet system is used and the lancet system in this position has the design shown in FIG. 1a.

In order to carry out the lancing operation, a plunger (not shown) of the lancing aid engages through the opening (7) into the lancet system where the plunger connects in a form-fitting manner with the arms (6) of the needle body. As a result the arms (6) are pressed together so that the lugs (12) of the arms (6) no longer engage in the recesses (14) and the needle can be moved forwards along the lancing direction (8). In this process the elastomeric protection (4) is firstly pressed against the lower wall (10) of the needle housing (2a). If the lancing operation is continued the needle is driven through the elastomeric protection and can thus emerge from the opening (9) in the lower wall (10) and produce a wound in the intended part of the body. The elastomeric protection (4) is meanwhile held back by the wall (10) as a result of which the front part (15) of the needle body (2*b*) corresponding to the recess (16) can move over the elastomeric protection. After the lancing operation has been carried out, the needle body (2*b*) and the needle are subsequently retracted into the protective portion (2*a*) due to the form-fitting coupling to the drive plunger. Once the rear arms (6) are in the rear protective portion of the needle housing (2*a*), the lugs (12) can engage in the recess (13) of the needle housing (2*a*) when the needle body (2*b*) is pulled back. The lancet system is now in a second resting position after the lancing operation. In this position the second part of the needle body (2*b*) protrudes from the opening (5) of the protective portion of the needle housing (2*a*) in such a manner that the needle body is deformed in this area. The tapered parts (5 and 5') no longer fit together. In a lancing aid designed in a corresponding manner which only allows insertion of a lancet system when the tapered part (5) of the needle body is completely formed according to FIG. 1*a*, insertion of an already used lancet system is blocked according to FIG. 1*c*.

The example shown in FIG. 1 has a blocking mechanism and enables the protective portion of the needle housing to be transferred to a first position during the lancing operation. When the lancet system is ejected after the needles have been used, the shape of the system has already been changed in such a manner that it is no longer possible to reinsert the lancet system in an appropriately designed lancing aid. Furthermore the needle tip is completely surrounded by the protective portion and hence there is no risk of injury for other persons e.g. during waste disposal.

FIG. 1 (*e*) is a perspective view of a lancet system illustrating a breaking of the needle housing when the lancet system is removed from the lancing aid. As described above, the blocking mechanism may include a predetermined breaking point which results in a breaking of the needle housing 2*a* when the lancet is removed from the lancing aid.

FIG. 2 shows a lancet system in the form of an essentially round lancet magazine. In comparison with FIG. 1 the protective portion of the needle housing (2*a*) is only designed as a magazine so that a plurality of needles (3) can be movably guided therein.

FIG. 2*a* shows an outer view of a magazine. The magazine housing which forms the protective portion is designed similarly to FIG. 1 and has recesses (13 and 14) into each of which the locking lugs (12) of the respective needle body (2*b*) can engage. The lancet system has a magazine axis (21) that is arranged concentrically in the protective portion and is used as a bearing for the lancet system in a lancing aid. The lancet system can be rotated around the axis (21) so that one needle in each case can be positioned relative to a drive unit (not shown) in the lancing aid. Like the lancet system shown in FIG. 1, the lancet system in FIG. 2 also has tapered parts (5) within the protective portion (2*a*) which are in the form of openings where the openings are also essentially tightly closed by the needle body (2*b*).

FIG. 2*b* shows a cross-section through the lancet magazine shown in FIG. 2*a*. The system has a similar structure to that of FIG. 1, but consists of a plurality of needles that are equipped with an associated needle body (2*b*). Consequently the lancet system shown in FIG. 2 has several parts which include an outer protective portion and several needle bodies 2(*b*). FIGS. 2*c* and 2*d* show the lancet system after use in which all needles of the lancet system have already been used for lancing. It is of course also possible that only some of the needles have already been used in the lancet system. In this case the needle body (2*b*) would only protrude through some of the openings (5) of the protective portion whereas the other openings would be tightly closed by the needle housing as shown in FIG. 2*a*. Depending on how the lancet system interacts with the lancing aid, embodiments are conceivable where reinsertion of the lancet system into a lancing aid is already blocked as soon as some of the needles have been used or is only blocked after all needles have been completely used in the lancet system. Advantageously it is also conceivable that the reinsertion of a partially used lancet system into the lancing aid is only possible when the system has been positioned relative to the drive plunger in such a manner that only unused lancets can be used by the system.

FIG. 3 shows a rectangular needle housing which also comprises a plurality of needles in the form of a magazine. The protective portion of the needle housing (2*a*) also has openings (9) in its lower end (10) from which the needles can emerge to perform a lancing operation. While in their resting position i.e. when no lancing operation is carried out, the needle tips of the needles (not shown) are within the protective portion of the needle housing (2*a*) in which the needles can be movably guided. The needle housing (2*a*) contains grooves in a lower portion (34) that borders the lower end (10) of the needle housing which make it easier to grip and thus facilitate its handling by the user. Recesses (33) are provided in this portion (34) as holding elements which, in an appropriately designed lancing aid, enable the lancet system to lock into the lancing aid during insertion. The blocking mechanism (31) is located in the middle of the needle housing (2*a*) as part of the needle housing (2*a*) and can be movably guided to an upper portion (35) of the needle housing (2*a*), and is firstly held in a starting position by spring-mounted arms (39). There is also a recess (32) in the upper part (35) which locks the blocking mechanism (31) when the blocking mechanism (31) is guided along the upper part of the needle body (35).

FIG. 3*b* shows the lancet system after use. As illustrated in FIG. 3*b*, the blocking mechanism (31) that surrounds the needle housing (2*a*) in the form of a ring is now positioned at the upper end of the needle housing so that the blocking mechanism (31) in this position widens the needle housing section (35). Once the blocking mechanism (31) has been locked into its position, it is no longer subsequently possible to reinsert the lancet system due to the enlarged needle housing.

FIGS. 3*c* and 3*d* illustrate in more detail the operation of the blocking mechanism (31) which is used in the lancet system described above. In order to lock the blocking mechanism (31) in the upper portion (35), the blocking mechanism has locking arms (36) which engage in the recesses (32). In the position shown in FIGS. 3*b* and 3*c* the locking arms (36) are spring-mounted against the lower edge of the recess (32) to secure the blocking mechanism (31) against displacement. The stop (37) also serves as an additional counter-flange of the blocking mechanism (31) against the projection (38) in the upper portion of the needle housing component (35). When the magazine is inserted as shown in FIG. 3*e* for first use in a lancing aid housing (70), the rear portion (35) of the magazine housing is positioned in an appropriately tapered position (82) of the housing (70). In contrast the front portion (80) of the housing (70) is widened so that the widened diameter of the lancet system due to the ring that acts as the blocking mechanism can be placed accordingly in the lancing aid housing. In this position the lancet system is held in the lancing aid in such a manner that a drive unit (not shown) of the lancing aid can engage in the magazine housing in order to couple onto a needle of the lancet system. The lancing aid housing also has two stops (83, 84) which are adjacent to the blocking mechanism (31) in this position of the lancet system in the lancing aid. If the lancet system is removed from the lancing aid housing after use, the stop (84) firstly has the effect that the blocking mechanism (31) remains fixed in position in the lancing aid housing while the magazine housing is pulled out of area (82) of the lancing aid. As a result the blocking mechanism (31) is pushed along the needle housing to the upper portion (35) of the needle housing. In this process the blocking mechanism (31) locks with the needle housing and the projection (38) and the stop (37) block further movement of the blocking mechanism along the needle housing. If the blocking mechanism (31) rests against the projection (38), a further pulling movement on the magazine housing overcomes the resistance of the stop (84) and the magazine can be removed from the lancing aid. The magazine is now outside the housing in a used state as shown in FIG. 3b where the blocking mechanism (31) is permanently positioned on the needle housing due to the locking hooks (36) and the stop (37). If the lancet magazine is reinserted into the lancing aid housing, the magazine can no longer be pushed into the tapered area (82) of the lancing aid due to the widened circumference of the upper section (35) of the needle housing. Hence it is no longer possible to position the lancet system in its original position in the lancing aid. The lancet system can no longer be held in the lancing aid. The coupling of individual needles to the drive unit of the lancing aid in order to carry out a lancing operation is blocked. Moreover after the lancet system has been ejected, the user can easily visually recognize that the lancet system is a used system due to the displaced ring. For this purpose it is also conceivable that the blocking mechanism (31) is highlighted in color.

As an alternative to the described change in the needle housing (2a), it is for example also conceivable that the blocking mechanism (31) can be moved over the recesses (33) of the lancet system. In this case a reinsertion of the lancet system in a lancing aid would be prevented because the lancet system could no longer lock into the lancing aid. Other embodiments using a movably mounted blocking mechanism are conceivable which for example result in a reduction in the size of the upper section (35) of the needle housing. In this case an unused lancet system e.g. in the state shown in FIG. 3b, is firstly placed in a lancing aid. A used lancet system would then be characterized in that the blocking mechanism (31) would have been pushed over the needle housing portion (35) in such a manner that the upper section (35) of the needle housing (2a) is diminished in size. FIG. 3a would thus represent the ejected state of the system. A correspondingly designed lancing aid would then for example have holding elements that could no longer interact with a lancet system that has been changed in this manner and reinsertion into the lancet system would no longer be possible. The locking elements of the blocking mechanism and of the needle housing (2a) would then have to be adapted accordingly. Furthermore it is also conceivable that a movable blocking mechanism (31) ensures that a reinsertion of the lancet system is blocked and also protects the needle tips. In this case the needle tips would not, as shown in FIG. 3, be retracted into a protective portion of the needle housing after the lancing operation. Hence the needle tips would not be automatically protected in a resting position. For example protection from the needle tips would not be ensured until the lancet system has been ejected from the lancing aid. According to the blocking mechanism shown in FIG. 3a, a movement of the blocking mechanism (31) elongates the needle housing in the area of the needle tips so that the needle tips are surrounded in a protective manner by the blocking mechanism and at the same time the blocking mechanism is activated due to a change in the shape of the housing. In this case a part of the needle housing acts as a blocking mechanism and also as a protective portion of the needle housing which surrounds the needle tip area when the lancet system is ejected. The protective portion of the needle housing and the blocking mechanism then comprise one structural element of the needle housing.

Figure 4:
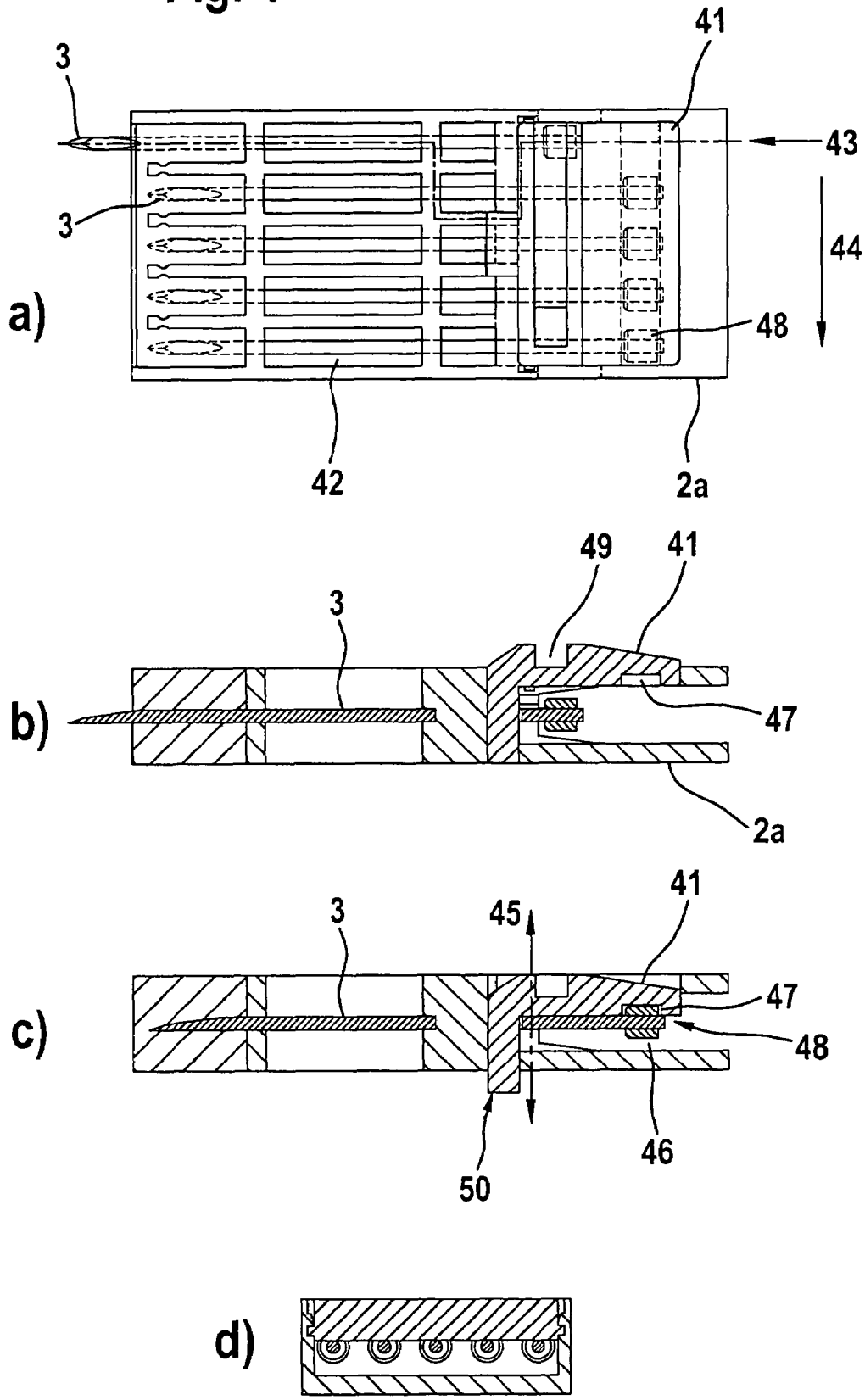
FIG. 4 (a) to FIG. 4 (d) is a perspective view of the Lancet system with a blocking mechanism which prevents a lancing aid from coupling to the lancet system.

FIG. 4 shows a rectangular lancet system in which several needles are positioned in chambers (42) of the protective portion of the needle housing (2a). The upper section of the protective portion of the needle housing has a blocking mechanism (41) in the form of a button which is located above the protective portion of the needle housing and can be moved along direction (45) towards the protective portion of the needle housing. The upper part of the button has a guide groove (49) which engages in a matching lip of the lancing aid (not shown) so that the lancet system can be securely positioned in the lancing aid. Once positioned in this manner, a drive plunger of the lancing aid (not shown) can couple with the rear area (48) of the needle (3) to carry out a lancing operation. For this purpose the needle is moved along direction (43) relative to the protective portion of the needle housing and the needle tip emerges from the protective portion (2a) of the needle housing. As in the systems that have already been described, the needles are returned to the magazine after the lancing operation and the needle tip is retracted within the needle housing (2a). The magazine is moved to the next position by moving the drive plunger of the lancing unit along direction (44) until the plunger can couple with a needle positioned in the adjacent chamber (42) in order to carry out a new lancing operation. If the lancet system has to be replaced in the lancing aid, the drive plunger must firstly be moved outside the rear area (46) of the needle housing (2a). For this purpose the magazine is moved to the next position and at the same time the button (41) is pressed down by a ramp on the housing of the lancing aid. The button (41) is now shifted within the lancet system as shown in FIGS. 4c and 4d so that the section (50) of the button protrudes from the bottom of the needle housing (2a). In this position a recess (47) of the button (41) engages the rear area (48) of the needle (3) which prevents the lancing aid from coupling again with the lancet system as shown in the front view of FIG. 4d. Hence a lancing operation cannot be carried out with a lancet system of FIG. 4c or d. Moreover the lancet system cannot be reinserted into the lancing aid due to the change in the shape of the needle housing in area (50). Hence the lancet system cannot be positioned via the guide groove (49) as part of a holding element.

Figure 5:
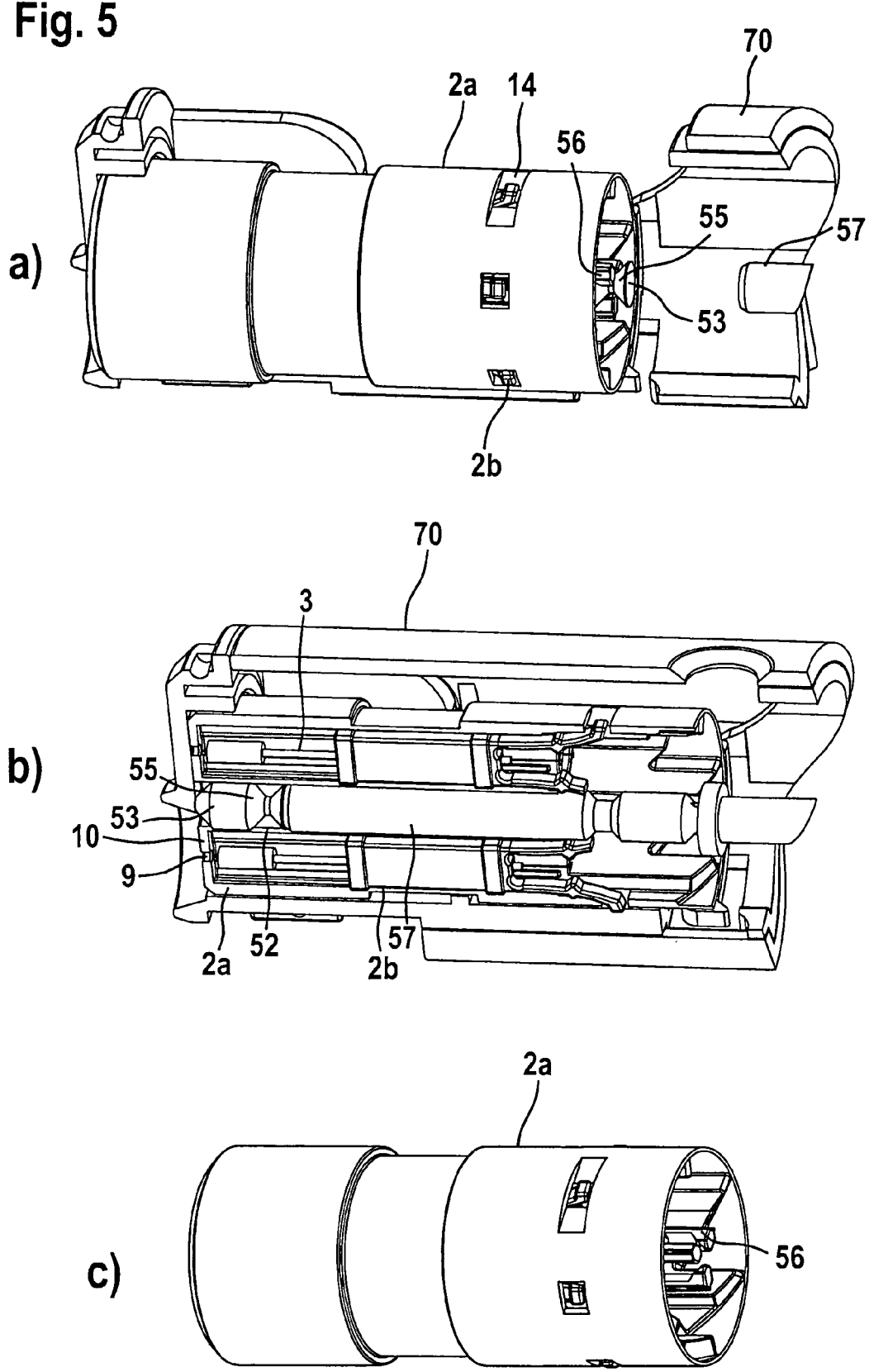
FIG. 5 (a) to FIG. 5 (c) is a perspective view of the Lancet system with a blocking mechanism which is activated when it is inserted in the lancing aid.

FIG. 5 shows a round-shaped lancet system which also contains several needles within the needle housing. Similarly to FIG. 2, the lancet system has a multipart needle housing. A channel (52) is arranged along the axis of rotation of the lancet system and a plug (53) is located in this channel at the upper end of the lancet system. The plug (53) is held in its first position by expanding holding arms (56) and this position represents the unused state of the lancet system. The holding arms (56) engage in a taper of the plug (53) which is formed by planes (55) of the plug which slant towards one another. When the lancet system is inserted into a lancing aid (70) the plug (53) is pressed within the channel (52) towards the needle tips by means of a centering plunger (57) of the lancing aid. The holding arms (56) are spread when the plunger is pressed in due to the slanting planes (55) of the plug (53). When the holding arms (56) of the lancet system are spread the plunger (57) can engage between them. Hence the plunger (57) can be almost completely inserted into the lancet system and is used as a bearing for and to position the magazine. An appropriately designed drive unit of the lancing aid can thus be oriented relative to the lancets of the system such that it can be coupled to a lancet and a lancing operation can be carried out. After the magazine has been used it is removed from the lancing aid. For this purpose the plunger (57) is pulled out from the interior of the magazine housing while the plug (53) remains at the lower end of the magazine in the area of the needle tips. Consequently a used lancet system is designed as shown in FIG. 5c in which the plug (53) is no longer held in the upper section of the holding arms (56). If an attempt is made to insert the used lancet system into the lancing aid, the plunger (57) strikes the upper portion (56) of the holding arms which in their unspread state prevent the plunger from penetrating into the lancet system. The absence of the plug (53) prevents the plunger (57) of the lancing aid from spreading the holding arms and thus the lancet system cannot be placed in the lancing aid.

Figure 6:
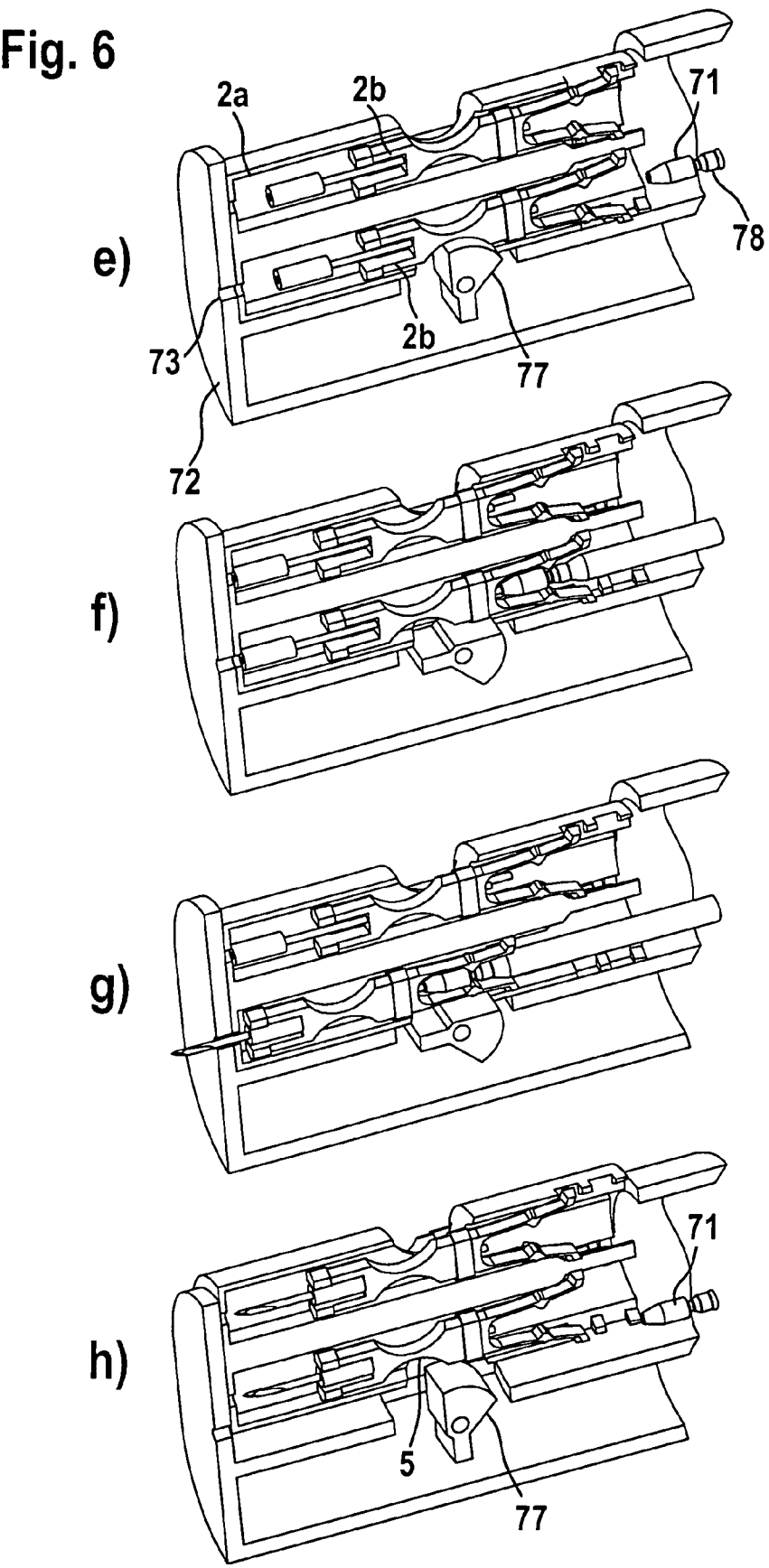
FIG. 6 (a) to FIG. (h) is a perspective view of the Lancing aid with a lancet magazine.

FIG. 6 shows another embodiment of a lancet system that is arranged within a lancing aid. FIGS. 6a to 6d firstly show a lancet system that is similar to that of FIG. 1. Like FIG. 1 the system shown in FIG. 6 also has an elastomer (4) which surrounds the needle tip in a sterile manner and a needle body and needle housing combination which has a taper (5, 5') in its middle. The needle body (2b) whose movement is guided in the interior of the protective portion of the needle housing (2a) also has arms (6) in its rear section which can couple in a formfitting manner with a plunger (78) of the lancing aid (72). As shown in FIGS. 6b and c, the plunger (78) engages with a head (71) in the needle body (2b) and moves the needle along the axis (8) in the direction of lancing. In this process the arms (6) of the needle body (2b) are pressed together and the projections (11) engage behind the notches in the head (71). The mode of operation of the lancet system is similar to that already described in FIG. 1 and is thus only shown again here with regard to its interaction with the lancing aid. The lancing aid (72) has a locking lever (74) that is mounted in the lancing aid and is rotatably pivoted on an axis (75). The locking lever (74) has a circular shape in a first area (77) such that the locking lever can engage in a form-fitting manner in the taper (5) of the lancet system.

FIG. 6a shows the state of the lancing aid with the lancet system before use in the inserted state. If it is intended to use the lancing aid for a lancing operation, the locking lever (74) is rotated by about 90° either automatically when a lancing operation is triggered or separately by the user, such that the lower section (77) of the locking lever no longer engages in the taper (5, 5'). The rotation of the locking lever is ensured by the fact that the lancing aid also has a depression (76) in the housing of the lancing aid which allows the locking lever to rotate around the axis of rotation (75). When the lancing operation is carried out, the needle body (2b) can move along the protective portion of the needle housing (2a) and a section of the needle body (2b) emerges from the opening of the needle housing (2a) without being hindered by the locking lever (74). In this process the needle tip is driven through the elastomer and the exit opening (9) of the lancet system and through an exit opening (73) of the lancing aid.

After the lancing operation the needle returns to its resting position during which, however, the needle body locks into the recess (13) of the protective portion of the needle housing. As already described in FIG. 1, this results in a change in the outer shape of the needle housing in the area of the taper (5) since the needle body (2b) now protrudes from the opening of the needle housing (2a). After the lancet system has been removed from the lancing aid, the locking lever (74) rotates back into its initial position as shown in FIG. 6a. As indicated in FIG. 5d, a reinsertion of the lancet system into the lancing aid is blocked by the locking lever (74). The locking lever (74) can no longer engage in the taper (5) of the used lancet system since the taper (5) is partially closed by the needle body (2b). Hence the lancet system can no longer be positioned and thus held in its original position. The plunger (78) can no longer engage in the lancet system. The head (71) and the projections (11) are prevented from forming a form-fitting connection.

FIGS. 6e-6h show embodiments similar to FIGS. 6a-6d in which the lancet system consists of a plurality of needles so that they can be stored in a magazine as shown in FIG. 2. The operating principles are, as already described, identical and can be simply transferred from the system with one needle to the system shown in FIGS. 5e-5h. At this point the intention is only to illustrate an embodiment that allows a magazine to be reinserted whose needles have only been partially used. For this the user must rotate the magazine relative to the lancing aid housing until the locking lever (74) can engage in a taper (5) which is not blocked by a needle body (2b). This positioning of the lancet system relative to the lancing aid and consequently relative to the drive plunger ensures that only a lancet that has not yet been used is employed for the next lancing operation. An advance of the lancet system in only one direction of rotation and a mechanism that allows no more than one rotation of the lancet system by 360° can be added as required in order to prevent already used lancing aids from being used again.

FIG. 7 shows another embodiment of a lancet system that is in the form of a round magazine housing. The needle housing design has several parts similar to the figures that have already been described. The sterile protection and needles are also arranged as already described and thus a more detailed description is omitted here. Similar to the system described in FIG. 5 the blocking mechanism shown in FIG. 7 is also actuated when the lancet system is inserted into the lancing aid. For this purpose the needle housing (2a) has a blocking mechanism (31) that is in the form of an outer ring that surrounds the upper section (35) of the needle housing. When positioned at this position the blocking mechanism (31) essentially covers the elastic arms (90) that are located in the upper portion of the needle housing (35). As a result the elastic arms (90) are pressed into the recess (95) of the needle housing (2a). The blocking mechanism (31) also has a circular protrusion at its lower end that enlarges the circumference of the needle housing (2a) at this position. If the lancet system is inserted into a lancing aid, the circumference of the lancing aid is selected such that the ring (96) cannot be inserted into the lancet system. The ring is pressed downwards relative to the needle housing into the area of the lancet tips when the lancet system is inserted into the lancing aid by means of a lower edge (97) acting as a counter-flange for the lancing aid housing. As a result the spring-mounted locking arms (90) are released from the ring. The resting arms are now in a spread state in the lancing aid and are pressed against the inner housing wall (98) of the lancing aid. When a used lancet system is removed from the lancing aid, the locking arms (90) slide along the sloping housing wall (98) in a tapered area of the lancing aid housing and are firstly pressed into the recess (95) of the needle housing due to the slanting wall (98). Hence the lancet system can be readily removed from the tapered area of the lancing aid. The used lancet system is subsequently present in a changed form as shown in FIG. 7c. When the system is reinserted into a lancing aid the locking arms (90) are now spread and thus the circumference of the needle housing (2a) is enlarged in the area (35) thus preventing an insertion of the lancet system into the front narrowed area of the lancing aid.

As any person skilled in the art will recognize from the previous description and from the figures and claims, modifications and changes can be made to the preferred embodi-

What is claimed is:

1. A multiple use lancing aid for producing an opening in the skin, the lancing aid comprising:
   a lancing aid housing for inserting a removable lancet system, wherein the lancing aid housing has a holding element that interacts with a holding element in the lancet system when the lancet system is positioned in the lancing aid housing;
   the lancet system comprising at least one needle having a needle tip and a needle housing, wherein the at least one needle is movably connected to the needle housing, wherein the needle housing comprises a protective portion such that the protective portion of the needle housing and the needle can be moved relative to one another;
   wherein the protective portion of the needle housing partially surrounds the needle tip in a first position;
   wherein the protective portion of the needle housing and the needle tip are arranged relative to one another in a second position in such a manner that the needle tip extends from the protective portion of the needle housing;
   an opening in the lancing aid housing, wherein the needle tip of the at least one needle can emerge from the lancing aid housing during a lancing operation; and
   a blocking mechanism comprised in the needle housing, wherein the blocking mechanism is actuated by an interaction with the lancing aid housing such that after removal of the lancet system from the lancing aid housing, the holding element of the lancing aid housing is prevented from interacting with the holding element of the lancet system, and reuse of the lancet system with the lancing aid after the lancet system is removed from the lancing aid is thereby prevented.

2. The lancing aid as claimed in claim 1, wherein the holding element of the lancing aid housing is prevented from interacting with the holding element of the lancet system in such a manner that after removal from the lancing aid housing, the lancet system cannot be reinserted into the lancing aid housing.

3. The lancing aid as claimed in claim 1, wherein the lancet system and the lancing aid housing each have several, and independently acting holding elements.

4. The lancing aid as claimed in claim 1, wherein the actuation of the blocking mechanism prevents an interaction of the holding elements of the lancet system with the lancing aid housing such that the lancet system can not be held and positioned in the lancing aid housing after it is removed.

5. The lancing aid as claimed in claim 1, wherein an interaction of the holding elements of the lancing aid housing and the lancet system is prevented in such a manner that the needle cannot be propelled.

6. The lancing aid as claimed in claim 1, wherein the actuation of the blocking mechanism spatially separates the holding elements when the lancet system is reinserted into the lancing aid housing.

7. The lancing aid as claimed in claim 1, wherein the blocking mechanism is actuated when the lancet system is removed from the lancing aid housing.

8. The lancing aid as claimed in claim 1, wherein the blocking mechanism is actuated when the lancet system is inserted into the lancing aid housing.

9. The lancing aid as claimed in claim 1, wherein the blocking mechanism is actuated during a lancing operation.

10. The lancing aid as claimed in claim 1, wherein the protective portion of the needle housing and the needle tip are moved relative to one another to the first position during the removal of the lancet system from the lancing aid housing.

11. The lancing aid as claimed in claim 1, wherein the first position of the protective portion of the needle housing is the same as the resting position.

12. A lancet system for insertion into a lancing aid, the lancet system comprising:
    at least one needle with a tip for producing a skin opening;
    a needle housing comprising a holding element that interacts with a holding element of the lancing aid when the lancet system is inserted into the lancing aid, wherein the needle housing is movably connected to the needle in such a manner that at least one protective portion of the needle housing and the needle can be moved relative to one another;
    wherein the protective portion of the needle housing at least partially surrounds the needle tip in a first position and in a second position, the protective portion of the needle housing and the needle tip are spatially separated from one another such that the needle tip extends from the protective portion of the needle housing, the protective portion of the needle housing being positioned in the first position when the lancet system is removed from the lancing aid; and
    the needle housing comprising a blocking mechanism movably connected thereto, wherein the blocking mechanism is actuated by an interaction with the lancing aid and wherein the actuation moves the blocking mechanism relative to the needle housing and changes the shape of the needle housing such that, after removal of the lancet system from the lancing aid, the holding element is prevented from interacting with the holding element of the lancing aid, wherein reuse of the lancet system with the lancing aid after the lancet system is removed from the lancing aid is prevented.

13. The lancet system as claimed in claim 12, wherein the actuation of the blocking mechanism changes the shape of the needle housing.

14. The lancet system as claimed in claim 12, wherein the needle housing comprises a magazine housing that contains a plurality of needles.

15. The lancet system as claimed in claim 12, wherein the blocking mechanism is actuated independently of the protective portion of the needle housing and the needle moving relative to one another.

16. The lancet system as claimed in claim 12, wherein the actuation of the blocking mechanism covers the holding element of the lancet system.

17. The lancet system as claimed in claim 12, wherein the shape of the needle housing comprises the holding element of the lancet system.

18. The lancet system as claimed in claim 12, wherein the actuation of the blocking mechanism breaks the needle housing when it is removed from the lancing aid.

19. The lancet system as claimed in claim 12, wherein the actuation of the blocking mechanism enlarges at least one area of the needle housing.

20. The lancet system as claimed in claim 12, wherein the actuation of the blocking mechanism reduces the size of at least one area of the needle housing.

21. A lancing aid, comprising:
    a lancing aid housing;
    a needle housing configured for insertion into the lancing aid housing and removal therefrom after use;
    a needle movably mounted to the needle housing, the needle having a tip for producing a skin opening;

the needle being movable from a first resting position in which the needle housing at least partially surrounds the tip, to a lancing position in which the tip is exposed for puncturing a body part, and to a second resting position in which the needle housing at least partially surrounds the tip, the needle occupying the second resting position when the needle housing is removed from the lancing aid housing;

the needle being movable to and from the lancing position multiple times after the needle housing is inserted into the lancing aid housing and before removal therefrom; and a blocking mechanism, actuation of which changes the shape of the needle housing and prevents reuse of the needle with the lancing aid after the needle housing is removed from the lancing aid housing.

22. The lancing aid of claim 21, wherein the blocking mechanism is actuated upon insertion of the needle housing into the lancing aid housing, the needle being movable to the lancing position to perform a lancing operation after the actuation of the blocking mechanism.

23. The lancing aid of claim 21, wherein the needle housing comprises a hole through which the needle tip emerges in the lancing position, the hole configured for alignment with a lancing opening in the lancing aid housing when the needle housing is inserted into the lancing aid housing.

24. The lancing aid of claim 21, wherein the needle housing comprises a magazine and the needle comprises a plurality of needles.

25. The lancing aid of claim 21, wherein the needle housing comprises a holding element configured to interact with the lancing aid housing upon insertion of the needle housing into the lancing aid housing, the actuation of the blocking mechanism preventing the interaction of the holding element with the lancing aid housing after the needle housing is removed from the lancing aid housing.

26. The lancing aid of claim 21, wherein the blocking mechanism comprises a ring surrounding and movable relative to the needle housing.

27. The lancing aid of claim 26, wherein actuation of the blocking mechanism causes the ring to move to a position which allows at least one area of the needle housing to enlarge.

28. The lancing aid of claim 27, wherein the enlargement takes place as or after the needle housing is removed from the lancing aid housing.

29. The lancing aid of claim 21, wherein the actuation of the blocking mechanism prevents the needle housing from being reinserted into the lancing aid housing after removal.

30. The lancing aid of claim 21, wherein the first and second resting positions are the same.

31. The lancing aid of claim 21, wherein the needle is configured to move between the second resting position and the lancing position multiple times after the needle housing is inserted in the lancing aid housing and before the needle housing is removed from the lancing aid housing, whereby the needle can be reused.

32. The lancing aid of claim 21, wherein the needle is configured to move between the second resting position and the lancing position multiple times after the actuation of the blocking mechanism.

33. The lancing aid of claim 27, wherein the at least one portion of the needle housing that is enlarged comprises a flexible arm that moves outwardly when the blocking mechanism is actuated.

34. A lancet system for insertion into a lancing aid, the lancet system comprising:

at least one needle with a tip for producing a skin opening;

a needle housing with a holding element that interacts with a holding element of the lancing aid when the lancet system is inserted into the lancing aid, wherein the needle housing is movably connected with the needle in such a manner that at least one protective portion of the needle housing and the needle can be moved relative to one another;

wherein the protective portion of the needle housing at least partially surrounds the needle tip in a first position and in a second position, the protective portion of the needle housing and the needle tip are spatially separated from one another such that the needle is released by the protective portion of the needle housing, the protective portion of the needle housing being positioned in the first position when the lancet system is removed from the lancing aid; and a blocking mechanism in the needle housing, wherein the blocking mechanism is actuated by an interaction with the lancing aid and changes the needle housing such that, after removal of the lancet system from the lancing aid, the holding element is prevented from interacting with the holding element of the lancing aid, wherein reuse of the lancet system with the lancing aid after the lancet system is removed from the lancing aid is prevented and the actuation of the blocking mechanism enlarges at least one area of the needle housing.

35. A lancet system, comprising:

a needle housing configured for insertion into a lancing aid and removal therefrom after use;

a needle movably mounted to the needle housing, the needle having a tip for producing a skin opening;

the needle being movable from a first resting position in which the needle housing at least partially surrounds the tip, to a lancing position in which the tip is exposed for puncturing a body part, and to a second resting position in which the needle housing at least partially surrounds the tip, the needle occupying the second resting position when the needle housing is removed from the lancing aid;

a blocking mechanism, actuation of which changes the shape of the needle housing and prevents reuse of the needle with the lancing aid after the needle housing is removed from the lancing aid; and wherein, the blocking mechanism comprises a movable ring surrounding the needle housing and actuation of the blocking mechanism causes the ring to move to a position which allows at least one area of the needle housing to enlarge.

36. The lancet system of claim 35, wherein the enlargement takes place as or after the needle housing is removed from the lancing aid.

37. The lancet system of claim 35, wherein the at least one portion of the needle housing that is enlarged comprises a flexible arm that moves outwardly when the blocking mechanism is actuated.

38. A lancet system, comprising:

a needle housing configured for insertion into a lancing aid and removal therefrom after use;

a needle movably mounted to the needle housing, the needle having a tip for producing a skin opening;

the needle being movable from a first resting position in which the needle housing at least partially surrounds the tip, to a lancing position in which the tip is exposed for puncturing a body part, and to a second resting position in which the needle housing at least partially surrounds the tip, the needle occupying the second resting position when the needle housing is removed from the lancing aid; and a blocking mechanism, actuation of which allows at least one area of the needle housing to enlarge, which prevents reuse of the lancet system with the lancing aid after the needle housing is removed from the lancing aid.

39. The lancing aid of claim 21, wherein the blocking mechanism is movably connected to the needle housing between a first position in which the needle can be used with the lancing aid and a second position in which, after removal of the lancet system from the lancing aid, use of the lancet system with the lancing aid is prevented.

40. The lancet system of claim 12, wherein actuation of the blocking mechanism uncovers or covers the holding element of the needle housing.

41. The lancet system of claim 12, wherein the holding element of the needle housing comprises a flexible arm member.

42. The lancet system of claim 34, wherein the needle housing comprises a magazine housing that contains a plurality of needles.

43. The lancet system of claim 34, wherein the blocking mechanism is actuated independently of the protective portion of the needle housing and the needle moving relative to one another.

44. The lancet system of claim 35, wherein the needle is movable to and from the lancing position multiple times after the needle housing is inserted into the lancing aid and before removal therefrom.

45. The lancet system of claim 35, wherein the blocking mechanism is actuated upon insertion of the needle housing into the lancing aid.

46. The lancet system of claim 35, wherein the needle housing comprises a magazine and the needle comprises a plurality of needles.

47. The lancet system of claim 38, wherein the enlargement takes place as or after the needle housing is removed from the lancing aid.

48. The lancet system of claim 38, wherein the at least one portion of the needle housing that is enlarged comprises a flexible arm that moves outwardly.

49. The lancet system of claim 38, wherein the blocking mechanism comprises a ring surrounding and movable relative to the needle housing.

50. The lancet system of claim 49, wherein actuation of the blocking mechanism causes the ring to move to a position which allows the at least one area of the needle housing to enlarge.

51. The lancet system of claim 38, wherein the actuation of the blocking mechanism prevents the needle housing from being reinserted into the lancing aid housing after removal.

52. The lancet system of claim 38, wherein the first and second resting positions are the same.

53. The lancet system of claim 38, wherein the needle is configured to move between the second resting position and the lancing position multiple times after the needle housing is inserted in the lancing aid housing and before the needle housing is removed from the lancing aid housing, whereby the needle can be reused.

* * * * *